US00PP24323P2

(12) United States Plant Patent
Beekenkamp

(10) Patent No.: US PP24,323 P2
(45) Date of Patent: Mar. 18, 2014

(54) ***BEGONIA* PLANT NAMED 'BKPBEELA'**

(50) Latin Name: *Begonia hiemalis*
Varietal Denomination: BKPBEELA

(75) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 14 days.

(21) Appl. No.: 13/507,634

(22) Filed: Jul. 13, 2012

(51) Int. Cl.
*A01H 5/00* (2006.01)

(52) U.S. Cl.
USPC ..... Plt./348

(58) Field of Classification Search
USPC ..... Plt./348, 347
See application file for complete search history.

*Primary Examiner* — Kent L Bell
(74) *Attorney, Agent, or Firm* — C. A. Whealy

(57) ABSTRACT

A new and distinct cultivar of *Begonia* plant named 'BKPBEELA', characterized by its broadly upright, somewhat outwardly spreading and mounded plant habit; moderately freely basal branching habit; medium-size leaves; uniform and freely flowering habit; and flowers that are salmon pink in color on both the upper and lower surfaces.

2 Drawing Sheets

Botanical designation: *Begonia hiemalis*.
Cultivar denomination: 'BKPBEELA'.

CROSS-REFERENCED TO CLOSELY RELATED APPLICATIONS

Title: *Begonia* Plant Named 'BKPBECSA' (U.S. Plant patent application Ser. No. 13/507,634).
Applicant: Annie Cornelia Beekenkamp.
Filed: Concurrently with this application.

BACKGROUND OF THE INVENTION

The present invention relates to a new and distinct cultivar of *Begonia* plant, botanically known as *Begonia hiemalis*, commercially referred to as a Elatior *Begonia* and hereinafter referred to by the name 'BKPBEELA'.

The new *Begonia* plant is a product of a planned breeding program conducted by the Inventor in Amstelveen, The Netherlands. The objective of the breeding program was to develop new freely branching and freely flowering *Begonia* plants with attractive foliage and flower colors.

The new *Begonia* plant originated from a cross-pollination made by the Inventor in September, 2006 of a proprietary selection of *Begonia hiemalis* identified as code number 06-289-03, not patented, as the female, or seed, parent with a proprietary selection of *Begonia hiemalis* identified as code number 6500604, not patented, as the male, or pollen, parent. The new *Begonia* plant was discovered and selected by the Inventor as a single flowering plant from within the progeny of the stated cross-pollination in a controlled greenhouse environment in Amstelveen, The Netherlands in November, 2007.

Asexual reproduction of the new *Begonia* plant by tip cuttings in a controlled greenhouse environment in Amstelveen, The Netherlands since August, 2008 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'BKPBEELA'. These characteristics in combination distinguish 'BKPBEELA' as a new and distinct *Begonia* plant:

1. Broadly upright, somewhat outwardly spreading and mounded plant habit.
2. Moderately freely basal branching habit.
3. Medium-size leaves.
4. Uniform and freely flowering habit.
5. Flowers that are salmon pink in color on both the upper and lower surfaces.

Plants of the new *Begonia* can be compared to plants of the female parent selection. Plants of the new *Begonia* differ primarily from plants of the female parent selection primarily in the following characteristics:

1. Leaves of plants of the new *Begonia* are glabrous whereas leaves of plants of the female parent selection are slightly pubescent.
2. Plants of the new *Begonia* and the female parent selection differ in flower color as plants of the female parent selection have yellow-colored flowers.

Plants of the new *Begonia* can be compared to plants of the male parent selection. Plants of the new *Begonia* differ primarily from plants of the male parent selection in the following characteristics:

1. Plants of the new *Begonia* have darker green-colored leaves than plants of the male parent selection.
2. Plants of the new *Begonia* have double type flowers whereas plants of the male parent selection have single type flowers.
3. Plants of the new *Begonia* have larger flowers than plants of the male parent selection.

Plants of the new *Begonia* can be compared to plants of the *Begonia* 'BKPBECSA', disclosed in U.S. Plant patent application Ser. No. 13/507,633. Plants of the new *Begonia* and 'BKPBECSA' differ primarily in the following characteristics:

1. Plants of the new *Begonia* flower about five days earlier than plants of 'BKPBECSA'.
2. Plants of the new *Begonia* are more freely flowering than plants of 'BKPBECSA'.

Plants of the new *Begonia* can also be compared to plants of the *Begonia* 'Peggy', disclosed in U.S. Plant Pat. No. 12,676. In side-by-side comparisons conducted in Amstelveen, The Netherlands, plants of the new *Begonia* differed from plants of 'Peggy' in the following characteristics:

1. Plants of the new *Begonia* were not as compact as plants of 'Peggy'.
2. Plants of the new *Begonia* were more freely flowering than plants of 'Peggy'.
3. Plants of the new *Begonia* and 'Peggy' differed in flower color as plants of 'Peggy' had dark pink and light yellow bi-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'BKPBEELA' grown in a container.

The photograph on the second sheet is a close up view of the upper and lower surfaces of typical flower buds, flowers and leaves of 'BKPBEELA'.

DETAILED BOTANICAL DESCRIPTION

Plants used for the aforementioned photographs and following observations and measurements were grown in 12-cm containers during the winter in a glass-covered greenhouse in Maasdijk, The Netherlands. During the production of the plants, day temperatures ranged from 19° C. to 20° C., night temperatures ranged from 18° C. to 19° C. and light levels averaged 7,000 lux. Plants were eleven weeks old when the photographs and the description were taken. In the following description, color references are made to The Royal Horticultural Society Colour Chart, 2007 Edition, except where general terms of ordinary dictionary significance are used.

Botanical classification: *Begonia hiemalis* 'BKPBEELA'.

Parentage:

*Female, or seed, parent.*—Proprietary selection of *Begonia hiemalis* identified as code number 06-289-03, not patented.

*Male, or pollen, parent.*—Proprietary selection of *Begonia hiemalis* identified as code number 6500604, not patented.

Propagation:

*Type.*—By tip cuttings.

*Time to initiate roots, summer and winter.*—About 20 days at temperatures of about 25° C.

*Time to produce a rooted young plant, summer and winter.*—About 35 to 36 days at temperatures of about 21° C. to 23° C.

*Root description.*—Medium in thickness, fibrous; light brown in color; plants of the new *Begonia* have not been observed to form tubers.

*Rooting habit.*—Moderate branching; medium density.

Plant description:

*Plant form and growth habit.*—Broadly upright, somewhat outwardly spreading and mounded plant habit; plant shape roughly globular; moderately freely basal branching with about four basal branches per plant; moderately vigorous growth habit.

*Plant height.*—About 17.9 cm.

*Plant width.*—About 27.1 cm.

*Branch description.*—Length: About 10.2 cm. Diameter: About 7 mm. Internode length: About 2 cm. Texture: Moderately pubescent. Aspect: Upright to about 30° from vertical. Color, developing: Close to 144A. Color, fully developed: Close to 146A.

*Leaf description.*—Arrangement: Alternate, simple. Length: About 8.9 cm. Width: About 7.8 cm. Shape: Broadly ovate to reniform. Apex: Broadly acute. Base: Oblique to hastate. Margin: Bi-serrate. Texture, upper surface: Smooth, glabrous; velvety. Texture, lower surface: Sparsely to moderately pubescent. Venation pattern: Palmate; reticulate. Color: Developing leaves, upper surface: Close to 147A tinged with close to N199A. Developing leaves, lower surface: Close to 183B. Fully expanded leaves, upper surface: Darker than between 139A and 147A; venation, close to 137B. Fully expanded leaves, lower surface: Close to 178A; venation, close to 146B. Petioles: Length: About 3.9 cm. Diameter: About 4 mm. Texture, upper and lower surfaces: Sparsely pubescent. Color, upper surface: Close to 146B, distally, strongly tinged with close to 182A. Color, lower surface: Close to 146B.

Flower description:

*Flowering habit.*—Double rotate sterile flowers arranged in axillary compound cymes; freely flowering habit with about 16 flowers per cyme and about 200 flowers developing per plant; flowers face upright to outwardly.

*Fragrance.*—None detected.

*Natural flowering season.*—Plants begin flowering about 65 days after planting; long flowering period, plants flower freely and continuously from spring until autumn in The Netherlands.

*Flower longevity.*—Individual flowers last about ten days on the plant; flowers not persistent.

*Inflorescence height.*—About 12.6 cm.

*Inflorescence diameter.*—About 10.3 cm.

*Flower diameter.*—About 5 cm.

*Flower height.*—About 1.8 cm.

*Flower buds.*—Length: About 2.1 cm. Diameter, flattened: About 2.1 cm. Shape, flattened: Orbicular. Color: Close to 43D; towards the apex, close to 43C; towards the base, close to 48D.

*Tepals.*—Quantity per flower and arrangement: About four in a single whorl. Length: About 3.2 cm. Width: About 3 cm. Shape: Broadly obovate to orbicular. Apex: Obtuse. Margin: Entire. Texture, upper and lower surfaces: Smooth, glabrous; slightly velvety. Color: When opening, upper surface: Close to 41C; towards the apex, close to 40C; towards the base, close to 41D. When opening, lower surface: Close to 47C. Fully opened, upper surface: Close to 48C; color does not change with development. Fully opened, lower surface: Close to 48C; margins, close to 48B; color does not change with development.

*Tepaloids.*—Quantity per flower and arrangement: About eight in about two whorls. Length: About 1.5 cm. Width: About 9 mm. Shape: Obovate. Apex: Obtuse. Margin: Entire. Texture, upper and lower surfaces: Smooth, glabrous; slightly velvety. Color: When opening, upper surface: Close to 41C. When opening, lower surface: Close to 48B. Fully opened, upper surface: Close to 43D; color does not change with development. Fully opened, lower surface: Close to 48C; color does not change with development.

*Peduncles.*—Length: About 6.8 cm. Diameter: About 4 mm. Angle: About 30° from branch axis. Texture: Smooth, glabrous. Color: Close to 152A.

*Pedicels.*—Length: About 1.9 cm. Diameter: About 2 mm. Angle: About 40° from the peduncle axis. Texture: Smooth, glabrous. Color: Close to N199C to N199D.

*Reproductive organs.*—Reproductive organ development has not been observed on flowers of plants of the new *Begonia.*

*Seeds and fruits.*—Seed and fruit development production has not been observed on plants of the new *Begonia.*

Disease & pest resistance: Resistance to pathogens and pests common to *Begonia* has not been observed on plants of the new *Begonia.*

Temperature tolerance: Plants of the new *Begonia* have been observed to tolerate temperatures from about 14° C. to about 35° C.

It is claimed:

1. A new and distinct *Begonia* plant named 'BKPBEELA' as illustrated and described.

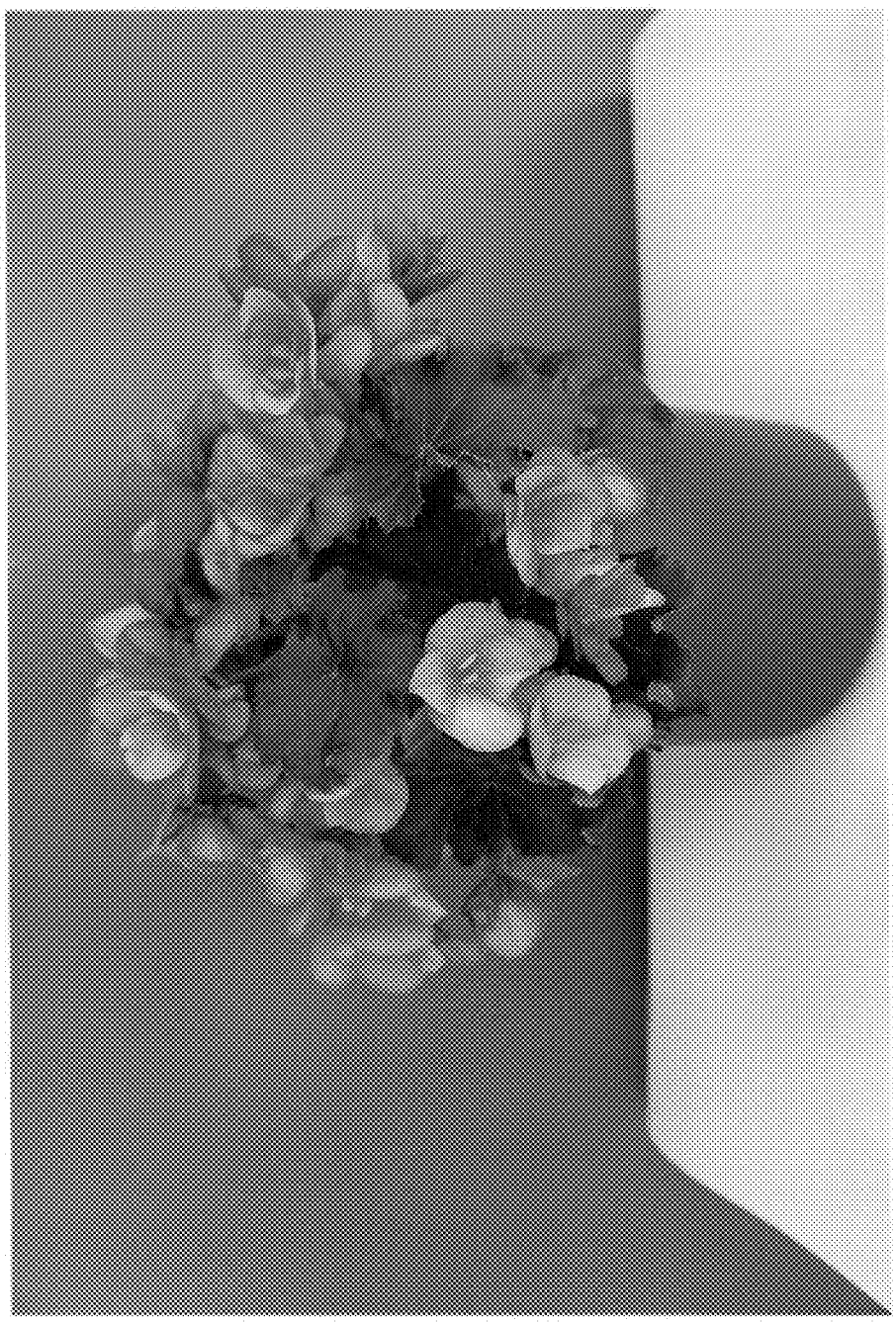

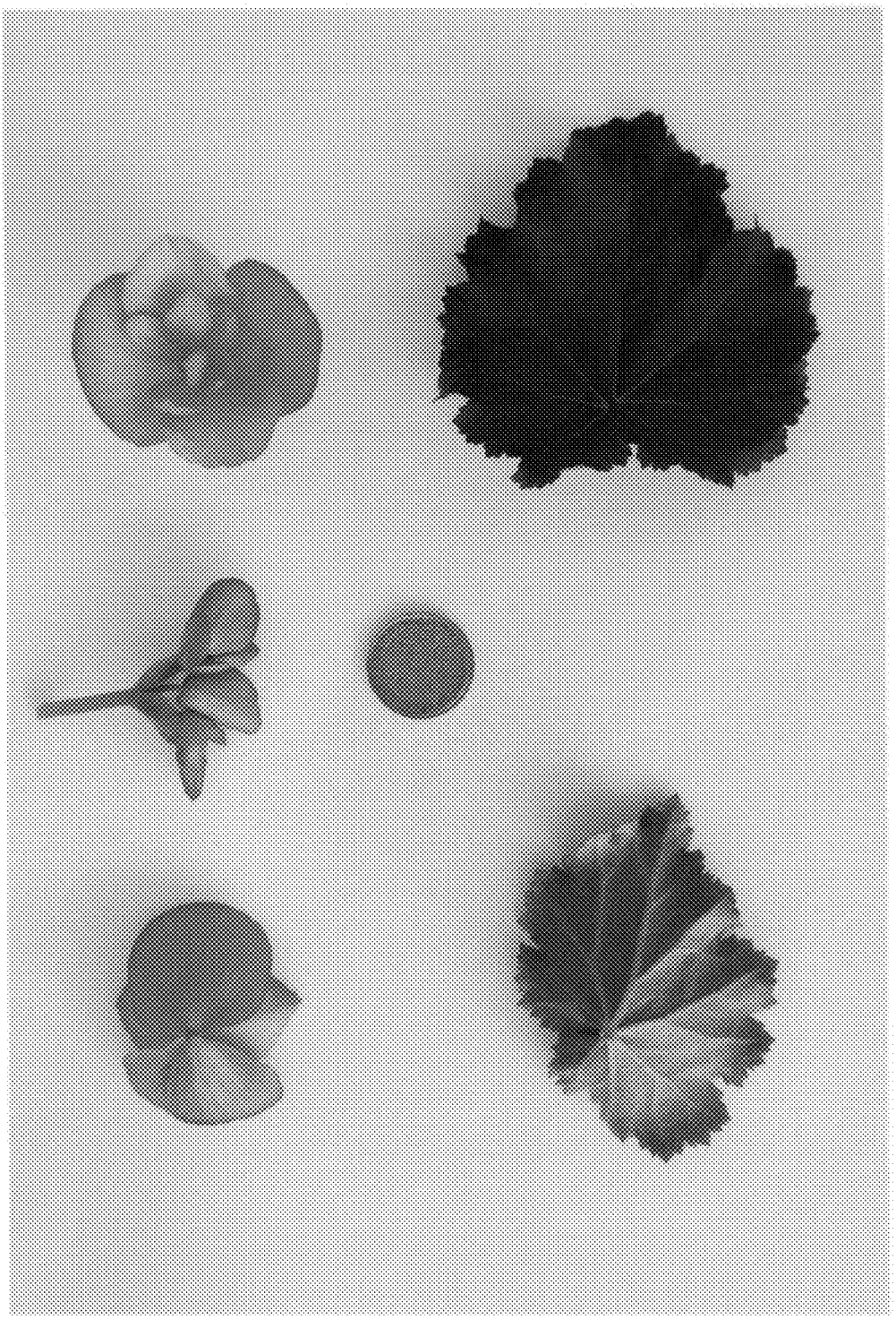

* * * * *